(12) United States Patent
Lane et al.

(10) Patent No.: US 12,078,623 B2
(45) Date of Patent: Sep. 3, 2024

(54) TECHNIQUES FOR DETERMINING ACTIVE INGREDIENT (AI) VOLATILITY FOR AGRICULTURAL SPRAY SOLUTIONS

(71) Applicant: Battelle Memorial Institute, Columbus, OH (US)

(72) Inventors: Timothy E. Lane, Upper Arlington, OH (US); Chris L. Scott, Columbus, OH (US); Brian Hopp, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 372 days.

(21) Appl. No.: 17/684,537

(22) Filed: Mar. 2, 2022

(65) Prior Publication Data

US 2022/0283130 A1 Sep. 8, 2022

Related U.S. Application Data

(60) Provisional application No. 63/156,311, filed on Mar. 3, 2021.

(51) Int. Cl.
| | |
|---|---|
| *G01N 30/72* | (2006.01) |
| *A01M 7/00* | (2006.01) |
| *H01J 49/04* | (2006.01) |
| *H01J 49/10* | (2006.01) |
| *G01N 30/02* | (2006.01) |

(52) U.S. Cl.
CPC ...... *G01N 30/7233* (2013.01); *H01J 49/0431* (2013.01); *H01J 49/105* (2013.01); *A01M 7/0014* (2013.01); *A01M 7/0092* (2013.01); *G01N 2030/027* (2013.01)

(58) Field of Classification Search
CPC .......... G01N 30/7233; G01N 2030/027; H01J 49/105; H01J 49/0431; A01M 7/0014; A01M 7/0092
See application file for complete search history.

(56) References Cited

U.S. PATENT DOCUMENTS 10,107,713 B2 * 10/2018 Spandl ............... G01M 9/04

OTHER PUBLICATIONS

Brusselman et al., "Wind Tunnel Evaluation of Several Tracer and Collection Techniques for the Measurement of Spray Drift", Commun Agric Appl Biol Sci 2004;69(4) 829-36) (Year: 2004).*

Fritz et al., "Evaluation of Spray Drift Using Low-Speed Wind Tunnel Measurements and Dispersion Modeling", Journal of ASTM International, vol. 7, No. 6, 2010 (Year: 2010).*

\* cited by examiner

*Primary Examiner* — David E Smith
(74) *Attorney, Agent, or Firm* — Grossman, Tucker, Perreault & Pfleger, PLLC; Edmund P. Pfleger

(57) ABSTRACT

Systems and methods of the present disclosure include the use of a tracer in agricultural spray solutions, and preferably a metal tracer, to determine if off-target drift of an active ingredient (AI) is based on drift caused during application or volatility of AI after application.

29 Claims, 9 Drawing Sheets

| Test | Spray Solution | Nozzle | $D_{v10}$ (μm) | $D_{v50}$ (μm) | $D_{v90}$ (μm) | %<141 (μm) |
|---|---|---|---|---|---|---|
| 1 | Fexapan + Liberty | | 56 | 118 | 235 | 63 |
| 2 | Fexapan + Liberty | XR11001 | 51 | 107 | 267 | 67 |
| 3 | Fexapan + PowerMAX | | 54 | 112 | 226 | 66 |
| 4 | Fexapan | | 108 | 269 | 543 | 17 |
| 5 | Fexapan + Liberty | TT11001 | 81 | 190 | 436 | 33 |
| 6 | Fexapan + PowerMAX | | 101 | 237 | 498 | 22 |

FIG. 2

| | Application | | | 24-hour Average | | |
|---|---|---|---|---|---|---|
| Test | Wind (mph) | Temp (c) | RH (%) | Wind (mph) | Temp (c) | RH (%) |
| 1 | 9.9 | 25.0 | 85.1 | 5.1 | 26.6 | 66.8 |
| 2 | 10.1 | 25.7 | 54.2 | 5.1 | 24.6 | 58.9 |
| 3 | 9.9 | 30.6 | 48.6 | 5.0 | 27.6 | 60.5 |
| 4 | 9.9 | 25.2 | 82.4 | 4.8 | 24.2 | 88.9 |
| 5 | 9.9 | 25.1 | 71.4 | 5.1 | 26.2 | 66.1 |
| 6 | 9.9 | 24.9 | 72.9 | 5.1 | 25.1 | 80.5 |

TECHNIQUES FOR DETERMINING ACTIVE INGREDIENT (AI) VOLATILITY FOR AGRICULTURAL SPRAY SOLUTIONS

This Application claims the benefit of U.S. Provisional Application Ser. No. 63/156,311, filed Mar. 3, 2021, which is hereby incorporated by reference in its entirety.

TECHNICAL FIELD

The following disclosure relates generally to agricultural spray solutions, and more particularly, to techniques for determining active ingredient (AI) drift caused by application versus drift caused by AI volatility.

BACKGROUND

Agricultural spray solutions can include pesticides used to control insects, plant diseases, snails, slugs, or weeds among others, and herbicides to kill undesirable weeds/plants.

Application of agricultural spray solutions can result in drift that leads to deposition in non-targeted areas. Drift can occur based on, for example, wind speed during application or through volatility of the active ingredient (AI) after application. Volatility of the AI can occur after application based on the AI converting to a gas and moving off application site. Conditions giving rise to volatility can vary depending on environmental factors such as temperature and humidity, and some agricultural spray solutions are designed with so-called "low-volatility" or "no-volatility" formulations to minimize or reduce the potential for volatility during application in a wide-range of potential temperature and humidity conditions.

It is incumbent on manufacturers and applicators of such agricultural spray solutions to understand an agricultural spray solutions potential for volatility in order to avoid potential damage to areas surrounding an application site. There exists a need to be able to differentiate between drift of an AI caused by application versus drift subsequent application caused by volatility.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are enlarged and positioned to improve drawing legibility. Further, the particular shapes of the elements as drawn are not intended to convey any information regarding the actual shape of the particular elements, and have been solely selected for ease of recognition in the drawings.

FIG. 2 illustrates an example table of observed droplet sizes (in μm) for six (6) different AI solutions used during the study described herein;

FIG. 3 illustrates a table of environmental conditions/ characteristics for the six (6) different test configurations used during the study described herein;

FIG. 10 illustrates a graph 1000 of the ratio of metal tracer to active ingredient amounts collected on the filter papers for the tests described above, taken after the application stage and before the volatility measurements for the study described herein.

DETAILED DESCRIPTION

Figure 1:
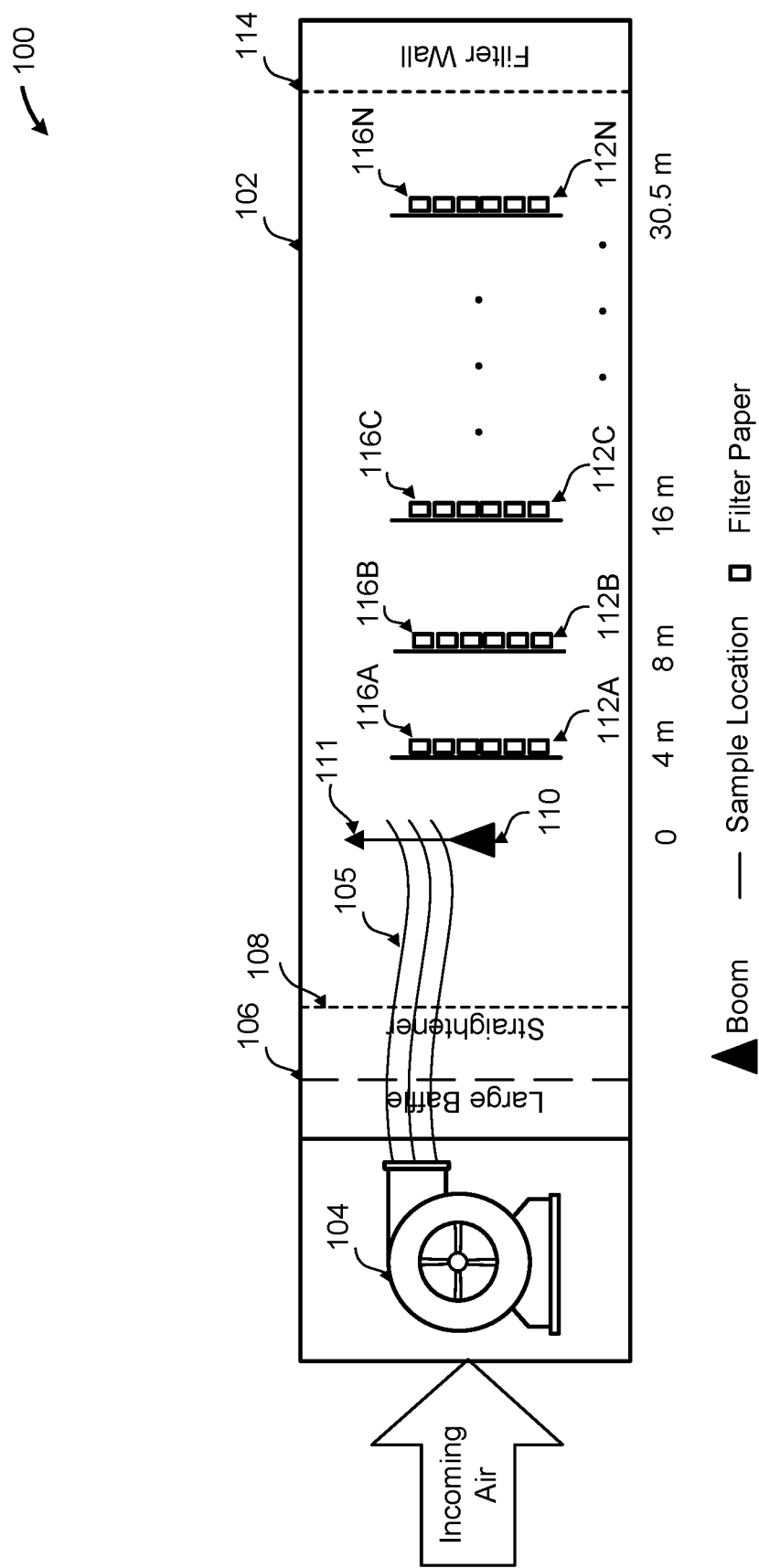
FIG. 1 illustrates an example AgDT consistent with aspects of the present disclosure.

Discerning whether movement of AI is generated by spray drift during application or volatility post application remains a challenge, and existing approaches such as field studies are complex, time-consuming, and expensive.

Systems and methods of the present disclosure include the use of a tracer in agricultural spray solutions, and preferably a metal tracer, to determine if off-target drift of an AI is based on drift caused during application or volatility of AI after application.

System and methods of the present disclosure preferably utilize an agricultural spray solution, which may be also referred to herein as simply a spray solution, with a predetermined ratio of AI to metal tracer. This disclosure has recognized that metal tracers are not subject to evaporation and can be utilized to determine whether an AI was collected as a droplet or vapor.

Systems and methods of the present disclosure further preferably utilize an agricultural drift tunnel (AgDT) that can be configured to regulate one or more environmental conditions to simulate a particular field application scenario. Some such environmental conditions include wind speed, wind direction, humidity, and temperature. Accordingly, an AgDT consistent with the present disclosure can include one or more sprayers/booms for projecting a spray solution, a blower for generating air flow/wind within the AgDT and optionally temperature control devices such as HVAC equipment for temperature and humidity regulation. Further, an AgDT consistent with the present disclosure can include one or more sample locations for measurement of spray solution deposition. Preferably, a plurality of sample locations are disposed within the AgDT at predetermined distances relative to the sprayer/boom. However, it should be noted that aspects and features of the present disclosure do not necessarily require the use of an AgDT and can be conducted via field tests, for example.

One example measurement process for implementation by an AgDT consistent with the present disclosure begins with generating airflow within the AgDT at a first wind speed via a blower for a first period of time, with the first period of time also being referred to herein as an application stage. The first wind speed is preferably in a range of 5 to 15 miles per hour (MPH), and more preferably at 10±0.5 MPH. Preferably, the blower displaces air in a direction that extends substantially parallel with a longitudinal axis of the AgDT. A sprayer/boom within the AgDT projects an amount of spray solution with a predetermined ratio of AI and tracer into the AgDT during the application stage. The predetermined ratio of AI to tracer is preferably in the range of 2.0:1 to 2.5:1, although other ratios are within the scope of this disclosure. Preferably, the sprayer is aligned with the blower such that the sprayer projects the spray solution along a direction that extends substantially transverse relative to the direction of the wind generated by the blower.

At the end of the application stage, the sprayer stops projection of the spray solution. Also at the end of the application stage, one or more filters disposed at predetermined sample locations within the AgDT may then be sampled to determine a baseline measurement, with baseline measurement indicating the ratio of AI to tracer projected during the application stage. Some preferred methods for determining the baseline measurement include liquid chromatography-mass spectrometry (LC-MS) to determine an amount of AI present in the one or more filters and inductively coupled plasma mass spectrometry (IC-MS) to determine an amount of tracer. Preferably, the baseline measurement is based on averaging measurements from a plurality of filters disposed at the predetermined sample locations within the AgDT, and/or a plurality of distances from the sprayer.

Following the application stage, the blower then preferably generates airflow within the AgDT at a second wind speed for a second period of time, which may also be referred to herein as a volatility measurement stage, a spray drift measurement stage, or simply a measurement stage. The second wind speed is preferably less than the first wind speed. One example second wind speed is in the range of 1 to 8 MPH, although other wind speeds during the volatility measurement stage are within the scope of this disclosure.

At the end of the volatility measurement stage, one or more collectors at the predetermined sample locations within the AgDT may then be sampled to determine a volatility measurement, with the volatility measurement indicating a ratio of the amount of AI present to tracer in the one or more collectors. In the event drift caused by volatility of the AI occurred, the ratio of AI to tracer will include a higher proportion of AI relative to the baseline measurement. For example, an applied spray solution having a predetermined ratio of 2:1 AI to tracer can result in a baseline measurement of substantially 2:1 (on average) of AI to tracer at the end of the application stage. Conversely, and for purposes of later discussion, the ratio may also be provided herein in reverse, e.g., tracer to AI. Thus, a ratio of AI to tracer that grows/increases relative to a baseline is indicative of AI volatility, and conversely, a ratio of tracer to AI that decreases relative to a baseline is indicative of AI volatility, and this disclosure may reference either ratio interchangeably.

In the event AI volatility occurs, the amount of tracer remains relatively constant while the amount of AI increases. For instance, one example is a ratio of 3:1 AI to tracer at the end of the volatility measurement stage. Accordingly, the increased amount/proportion of AI measured at the end of the volatility measurement stage relative to the baseline measurement can be attributed to AI volatility rather than drift. On the other hand, measurements where the ratio of AI to tracer remains relatively constant between the measurement and volatility stages can indicate a lack/absence of AI volatility.

Turning to the figures, FIG. 1 illustrates an example AgDT 100 consistent with aspects of the present disclosure.

As shown, the AgDT 100 includes a housing 102 that extends from a first end to a second end along longitudinal axis. The housing 102 is preferably a structure that includes sidewalls and roof to provide an enclosed space (See e.g., FIGS. 2-3).

The housing 102 further preferably includes a blower 104 at the first end to receive air from the surrounding environment and introduce an airflow 105 within the housing 102 at a target/selected wind speed. The blower 104 is preferably configured to provide the airflow 105 along a path/direction that extends substantially parallel with the longitudinal axis of the housing 102. The first end of the housing 102 may also be referred to as an inlet end. In the preferred example of FIG. 1, the housing 102 further includes a baffle 106 disposed adjacent/downstream from the blower 104. The baffle 106 can be implemented as a wall with perforations to cause a pressure drop and may also be referred to herein as a baffle plate. Following the baffle 106, the housing 102 further preferably includes a straightener 108. The straightener 108 can be implemented as a one (1) foot thick, two (2)-inch PVC tube wall, for example. The PVC tubes can force air to flow straight through the tubes, reducing the turbulence present in the air exiting the blower 104.

The housing 102 further preferably includes a sprayer 110 disposed adjacent the first end of the housing 102. The sprayer 110 can be implemented as a boom sprayer or other sprayer device such as a drone-mounted sprayer, airblast orchard sprayer, backpack sprayers, electrostatic sprayers, or any other suitable device. The sprayer 110 further preferably includes a nozzle/outlet that is configured to project spray solution along a path 111 that extends substantially transverse with path/direction of the airflow 105.

The sprayer 110 is further fluidly coupled to a spray solution tank/reservoir (not shown). The spray solution tank can include a predetermined amount of spray solution for application within the housing 102, and preferably, a mix of the spray solution that includes a predetermined ratio of AI to tracer.

In one preferred example, the spray solution includes a predetermined ratio of AI to metal tracer. In this example, the ratio of AI to tracer is in a range of 2.0:1.0 to 3.0:1.0. The AI of the spray solution can comprise a herbicide such as 3,6-dichloro-2-methoxybenzoic acid (Dicamba). The Dicamba can be provided as a Diglycolamine salt or a Dimethylamine salt. The tracer preferably comprises a metal, and more preferably, a metal salt such as Cesium Chloride (CsCl). Other metal tracers such as sodium (Na), Potassium (K), Rubidium (Rb), and Francium (Fr) are also within the scope of this disclosure for use as a tracer. In some embodiments, rarer metals (and/or rarer metal salts) are used (e.g., CsCl) to avoid detection of background metals (and/or salts that are more common, such as NaCl.

The housing 102 further preferably includes at least one sample location following the sprayer 110, and more preferably, a plurality of sample locations. As shown the example of FIG. 1, the housing 102 includes a plurality of sample locations 112A, 112B, 112c, . . . , 112n, with each sample location disposed at predetermined distance from the sprayer 110, for example, at 4 meters (m), 8 m, 16 m and 30.5 m from the sprayer 110. Each sample location of the plurality of sample locations 112A, 112B, 112C, . . . , 112n preferably includes one or more sample devices, e.g., 116A, 116B, 116C, . . . , 116n for the collection of the spray solution, e.g., following an application and volatility measurement stage. In one example, each sample device 116A, 116B, 116C, . . . , 116n includes at least one filter for collecting spray solution and determining a baseline measurement following an applications stage. The at least one filter is preferably implemented as a paper type filter such as a Whatman Grade 1 150 mm-type filter.

Continuing the previous example, each sample location of the plurality of sample locations 112A, 112B, 112C, . . . , 112n further preferably include at least one collector, which may also be referred to herein as sampler devices. The at least one collector is preferably implemented as a Polyurethane Foam (PUF) collector/sampler. The at least one collector further preferably fluidly couples to a vacuum pump (not shown) to generate suction at an orifice during the volatility measurement stage. In one preferred example, the vacuum pump generates suction in a range of 1.0 liters-per-minute (LPM) to 5.0 LPM, or at least 1.0 LPM. In one preferred example, the housing 102 includes a plurality of such collectors, with each collector of the plurality of collectors being disposed at a corresponding sample location. In this example, the vacuum pump is preferably fluidly coupled to each collector of the plurality of collectors and is configured to generate a substantially equal amount of suction at an orifice of each of the plurality of collectors.

In one preferred example, each sample location of the plurality of sample locations 112A, 112B, 112C, . . . , 112n within the housing 102 includes at least one filter disposed adjacent at least one collector. The at least one filter is preferably disposed at a predetermined distance from a ground surface within the housing 102. In one example, the at least one filter is disposed directly on the ground surface within the housing 102. The at least one filter is preferably also disposed at a second predetermined distance at least one adjacent collector. Preferably, the first predetermined distance between the ground surface and the at least one filter is less than the second predetermined distance between the at least one filter and the at least one adjacent collector. In one preferred example, the at least one filter is disposed below the at least one adjacent collector such that the at least one filter is disposed between the at least one adjacent collector and the ground surface within the housing 102. In this example, the vertical distance between the at least one filter and the at least one adjacent collector is at least 12 inches, although other vertical distances are within the scope of this disclosure.

Following the sample locations, the housing 102 further preferably includes a filter wall 114 disposed at the second end of the housing 102. The filter wall 114 can be configured to prevent spray solution from exiting the housing 102 while allowing a substantial portion of the airflow 105 to exit from the housing 102 unobstructed via the second end, which may also be referred to herein as an outlet end.

The following describes one example study conducted utilizing the AgDT 100. Overall, the spray drift versus volatility comparison determined during the study yielded favorable results and demonstrated the viability of the systems and methods disclosed herein relative to other approaches such as field studies. The technical objective for the study was to compare the spray drift and volatility from a boom application using a spray solution that contained an active ingredient and metal tracer. Spray boom application of formulations is a common method to apply products to field crops, and typically yields the potential for downwind drift both during and after application. As previously discussed, off-site movement of active ingredients have been a concern for agro-chemical registrants/companies, farmers, and the EPA. As new products enter the commercial market, costly field studies are required for drift associated with the application process and any volatility related drift post-application.

The study included employment of metal tracers to determine whether an AI is collected as a droplet or a vapor caused by AI volatility (which may also be referred to herein as volatile vapor), since the metal tracer does not evaporate, as discussed above. The AgDT 100 was utilized to provide a constant and uniform wind speed to simulate field applications.

In more detail, the approach utilized by the study to quantify and characterize the spray drift versus volatility uncertainty for a given sample was to apply a metal tracer to the tank mixture, which contains the AI. Cesium chloride (CsCl, Sigma-Aldrich®, 99.9% pure anhydrous, free flowing, ReagentPlus®) metal tracer was used in the study. Addition of cesium chloride can be used to determine whether the AI is collected as a droplet or a vapor, since the cesium chloride metal tracer in the formulation does not evaporate.

For this study, Dupont™ FeXapan™ herbicide plus VaporGrip™ was the baseline dicamba product which contains 42.8% Diglycolamine salt of dicamba 3,6-dichloro-o-anisic acid. The FeXapan™ had an application rate of 22 oz/Acre and was applied during an application stage with an overall spray volume of 15 gallons/Acre.

Two additional spray solutions were projected during the application stage that utilized Liberty® 280 SL herbicide (at an application rate of 32 oz/Acre) and Roundup PowerMax® herbicide (at an application rate of 32 oz/Acre) to increase the volatility of the dicamba.

Three total formulations, each containing 12.03 g of dicamba and 30.03 g of Cs+ ions (yielding a 2.5 Cs+ to dicamba ratio), were applied during the application stage using a traversing spray boom 110 containing six (6) nozzles. Each nozzle was spaced at 20″ along the length of the boom 110 and operated at 40 PSI during the application stage. The Teejet® XR11001 extended range flat spray nozzles and Turbo Teejet® TT11001 wide angle flat spray nozzles were selected for the application of the 3 formulations. The traversing mechanism was situated such that the direction of the application was perpendicular/transverse to the wind direction generated by the blower, e.g., blower 104. The boom traversed at 2 mph across the tunnel (1 pass), with the nozzles 2-feet above the floor, applying the tank mix to a layer of topsoil to mimic a field environment.

The AgDT 100 for this study was a 12×16×208 ft tunnel containing a 120,000-cfm blower to force ambient air through the tunnel. The 8-feet high by 15-feet wide inner working volume within the AgDT 100 along the 130-feet length permitted drift collection following the application stage.

During both the application stage and volatility measurement stage a uniform airflow was generated within the AgDT 100 and allowed for accurate determination of spray drift and volatility by maintaining a constant wind speed and direction. The wind speed during the application stage was set at ~10 mph, while the wind speed was set to 5 mph during the volatility measurement stage.

Following the application stage, filter paper deposition was determined to have similar metal-to-AI ratios as the tank mixtures when averaged across all sample locations. Following the volatility measurement stage, the PUF samplers were sampled and found to have a ratio of AI to tracer that indicated higher levels of dicamba than could be attributed to spray drift, which indicated volatilized dicamba vapor was also collected. This study highlighted the ability to discern droplet drift from volatility based on as few as a single application and volatility measurement stage.

In more detail, filter papers were placed at a plurality of sample locations downwind from the boom 110, with each sample location (such as sample location 112A) being a predetermined distance downwind of the boom 110 for collection droplet deposition (e.g., 4, 8, 16, and 30.5 meters). The filter papers were configured for collection of spray droplets that drifted and deposited on a ground surface of the AgDT 100 during the application stage.

Polyurethane foam (PUF) samplers/collectors were placed above an adjacent filter paper to capture airborne droplets during application and volatized vapors post application during the volatility measurement stage. The PUF samplers were placed 1-foot above adjacent filter papers to capture aerosol and volatile vapor. Vacuum pumps generated flow through each PUF sampler using critical flow orifices to achieve a ~1.8 lpm flow at each sample location.

Following the application stage, filter papers were collected for deposition quantification and removed from the AgDT 100 (e.g., after ceasing projection of the spray solution by the boom). The PUF samplers continued to sample over a period of 24 hours with the AgDT operating at a reduced 5 mph wind speed to promote the transfer of dicamba vapors from the application area to the downwind PUF samplers. Accordingly, the volatility measurement stage was 24 hours such that the PUF samplers were collected/sampled 24-hours post application of the AI.

Both filter papers and PUF samplers were analyzed for dicamba using LC-MS methodology and Cs+ ion content using ICP-MS techniques. Drift was determined for each of the three (3) formulations using both nozzles, for a total of six (6) test conditions (see the tables of FIGS. 2 and 3, described below).

Overall, the spray drift to volatility comparison showed favorable results. Filter paper deposition illustrated the initial 2.5 metal-to-active ingredient ratio when averaged across all samples. The PUF samplers were averaged and found to have a ratio which indicated higher levels of dicamba than could be attributed to spray drift, indicating volatilized dicamba was also collected.

The outcome of this study, based on only single repetitions, highlighted the ability to discern droplet drift from volatility utilizing a metal tracer. Thus, an AgDT which features the use of a tracer within the spray solution achieves a relatively low-cost method and time saving solution that can accurately determine the presence of volatile vapor relative to drift during application without necessarily performing costly field studies.

FIG. 2 illustrates an example table 200 of observed droplet sizes (in μm) for six (6) different AI solutions used during the study discussed above. Column 202 lists the AI solutions used for the XR11001 (Column 204) nozzle (tests 1-3) and the TT11001 nozzle (tests 4-6). The AI solutions included Fexapan alone, Fexapan+Liberty, and Fexapan+PowerMAX. Columns 206 illustrate the percentile of droplet sizes in the $10^{th}$ percentile, $50^{th}$ percentile and $90^{th}$ percentile, while column 208 illustrates the standardized parameter of the percent of spray volume that included droplet sizes less than 141 μm.

FIG. 3 illustrates a table 300 of environmental conditions/characteristics for the six (6) different test configurations used during the study discussed above. Columns 302 illustrate wind speed, temperature and relative humidity during the spray application stage of the test, conducted for a few seconds (1-3 seconds) to simulate field application of the AI solutions. Columns 304 illustrate wind speed, temperature and relative humidity during the volatility stage of the test (over 24 hours).

Figure 4:
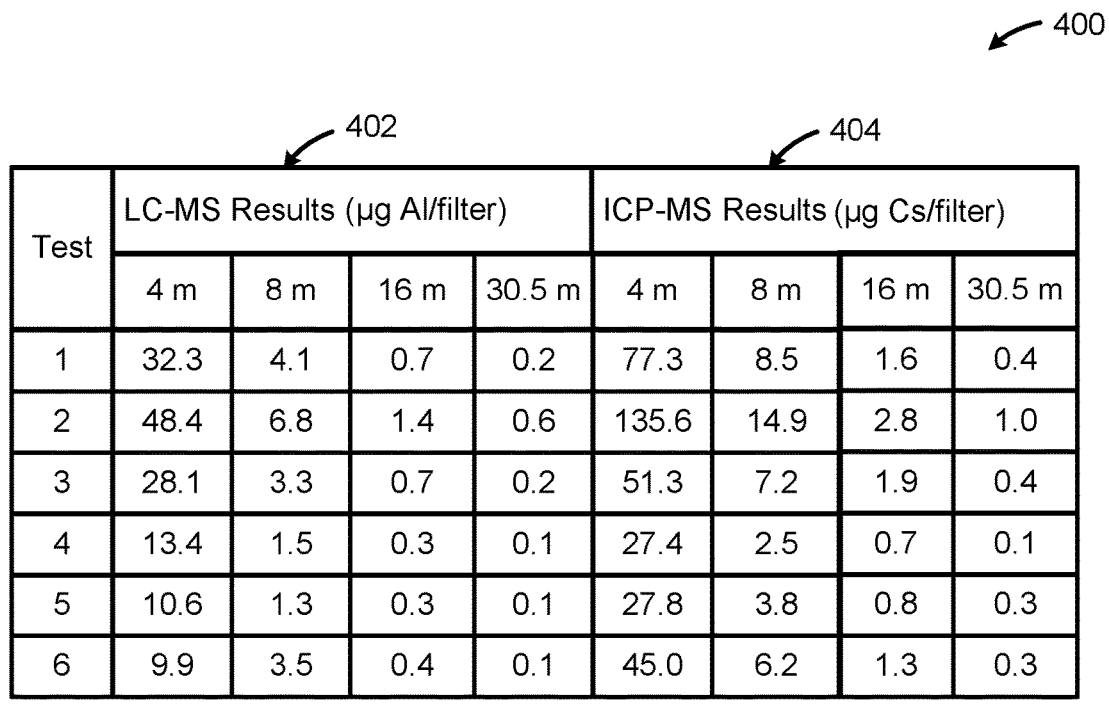
FIG. 4 illustrates a table of measurement results from the plurality of sample locations within the AgDT after the application stage of the study described herein.

FIG. 4 illustrates a table 400 of measurement results from the plurality of sample locations within the AgDT 100 after the application stage of the study discussed above. Columns 402 represent the sample data for the AI solution collected at m., 8 m., 16 m., and 30.5 m. following the application stage, and prior to the volatility measurement stage. Columns 404 represent the sample data for the metal tracer (Cs) collected at m., 8 m., 16 m., and 30.5 m. following the application stage, and prior to the volatility measurement stage.

Figure 5:
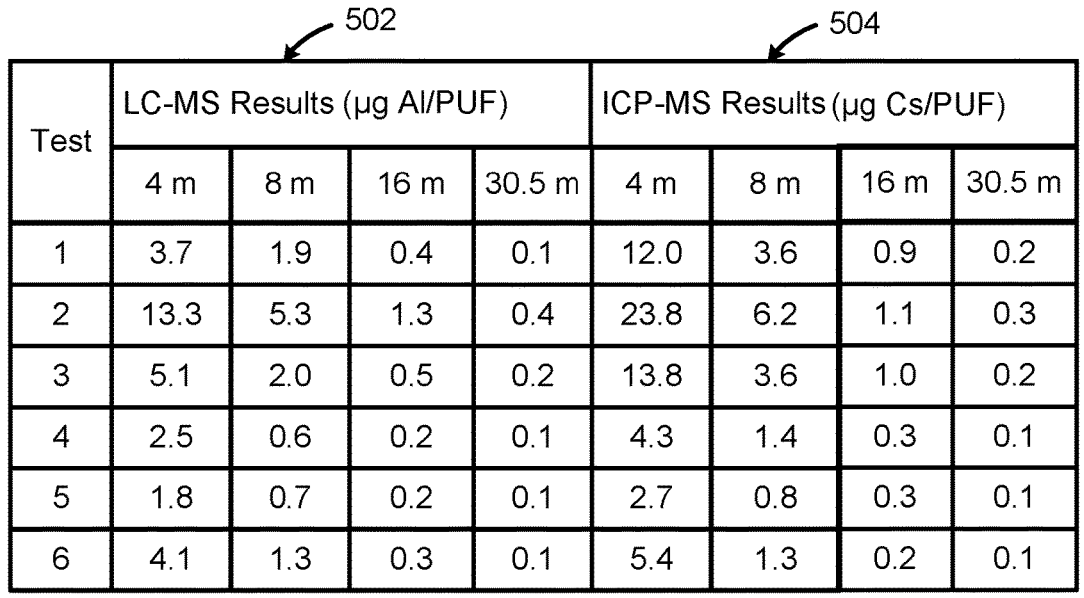
FIG. 5 illustrates a table that provides measurement results from the plurality of sample locations within the AgDT after volatility stage (24 hrs.) of the study described herein.

FIG. 5 illustrates a table 500 that provides measurement results from the plurality of sample locations within the AgDT 100 after volatility stage (24 hrs.) of the study discussed above. Columns 502 represent the sample data for the AI solution collected at m., 8 m., 16 m., and 30.5 m. following the volatility stage (24 hrs.). Columns 504 represent the sample data for the metal tracer (Cs) collected at m., 8 m., 16 m., and 30.5 m. following the volatility stage.

Figure 6:
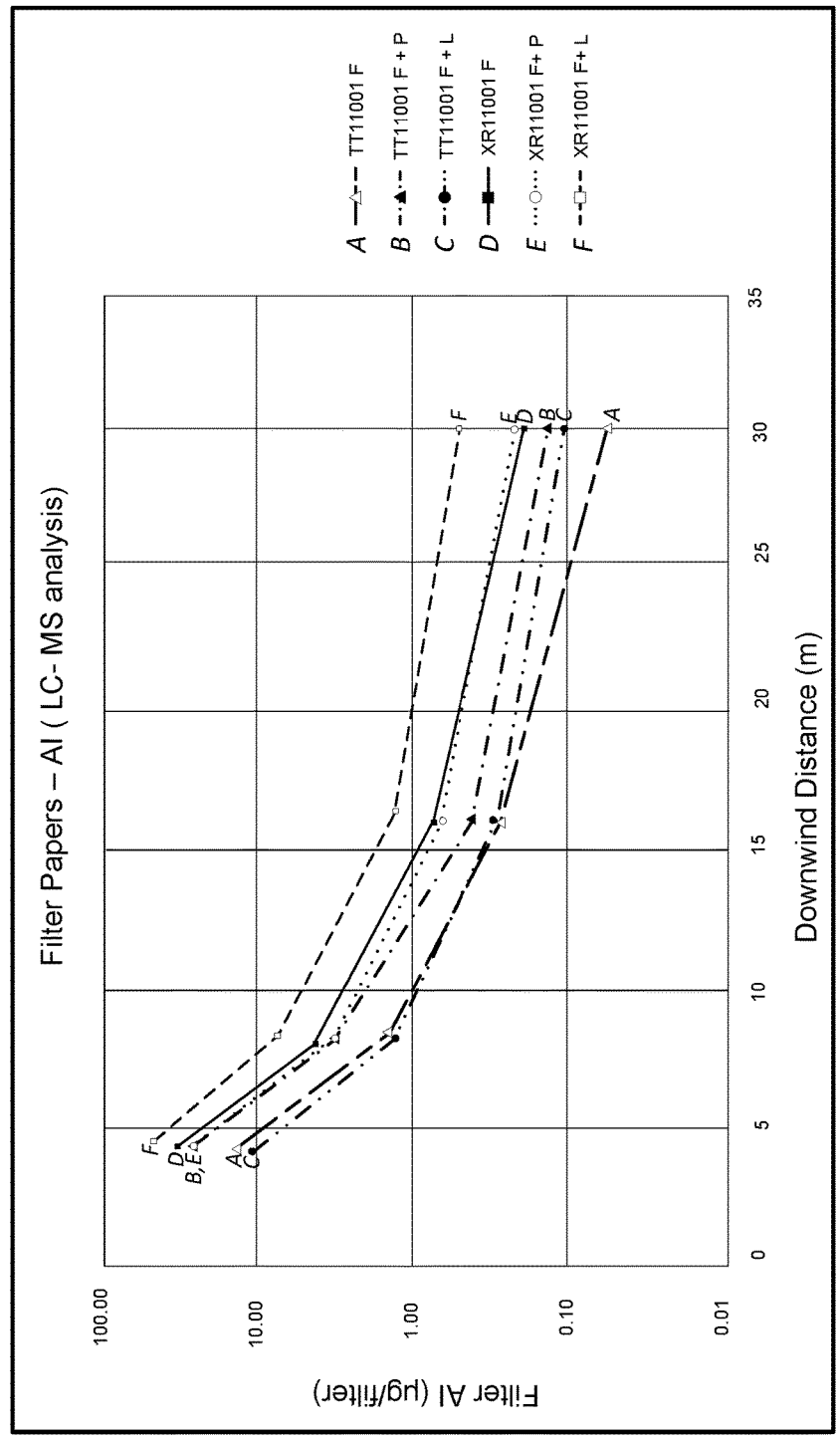
FIG. 6 illustrates a graph 600 of the amount of active ingredient (AI) deposited on the filter papers following an application stage of the study described herein.

FIG. 6 illustrates a graph 600 of the amount of active ingredient (AI) deposited on the filter papers following an application stage consistent with the present disclosure. The plot points illustrated in the graph 600 are taken from the data points illustrated in the table 400 of FIG. 4. The results confirmed what was expected for the different nozzle/formulation combinations tested. That is, smaller droplets have more drift (e.g., higher concentrations farther downwind). The XR10001 nozzle yields a smaller droplet size than the TTI11001 nozzle. The addition of PowerMax herbicide or Liberty herbicide also tend to decrease the size of the droplets compared to FeXapan mixed by itself.

Figure 7:
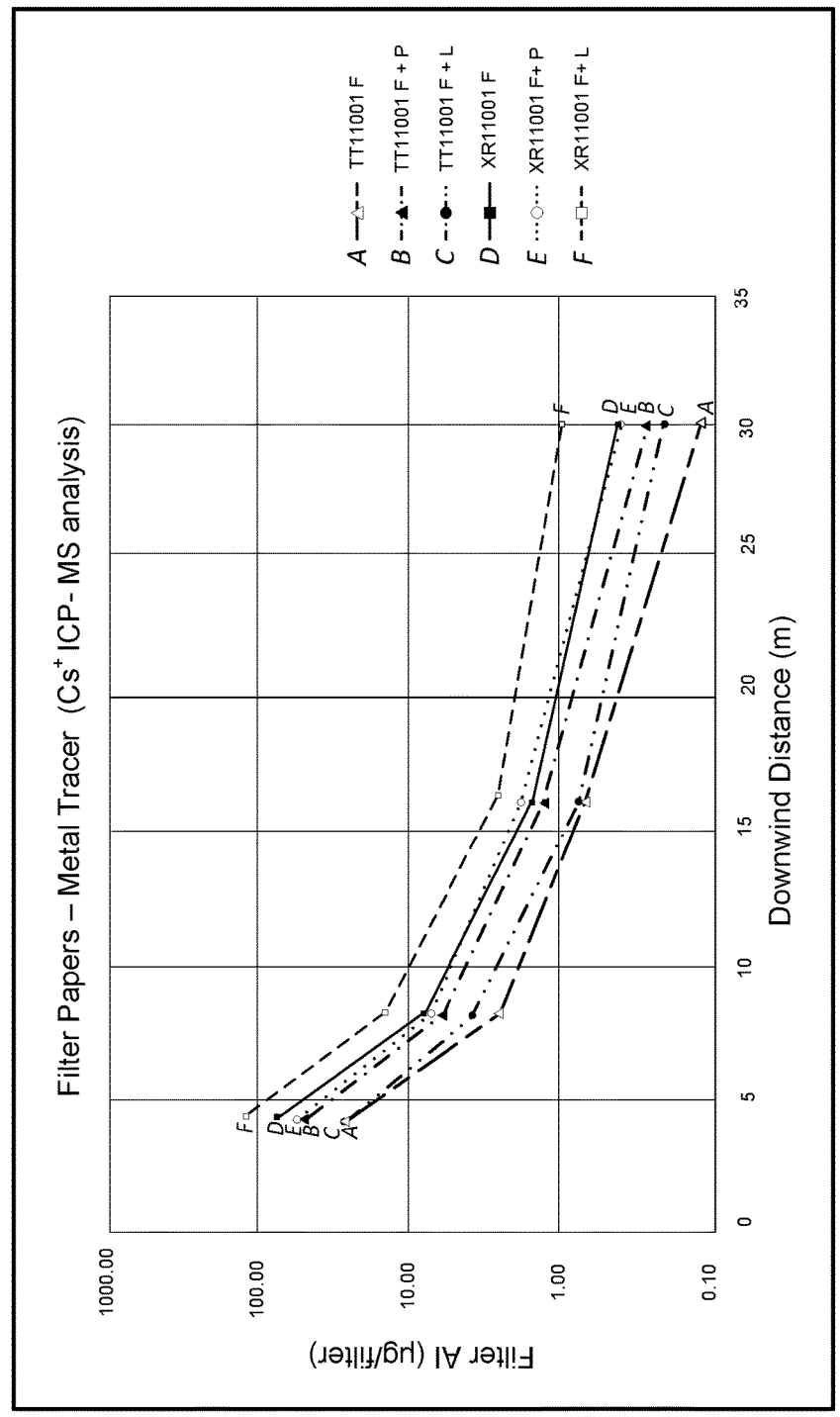
FIG. 7 illustrates a graph of the amount of metal tracer (Cs) deposited on the filter papers following an application stage consistent of the study described herein.

FIG. 7 illustrates a graph 700 of the amount of metal tracer (Cs) deposited on the filter papers following an application stage consistent with the present disclosure. The plot points illustrated in the graph 700 are taken from the data points illustrated in the table 400 of FIG. 4. The trends are consistent with the results shown in FIG. 7.

Figure 8:
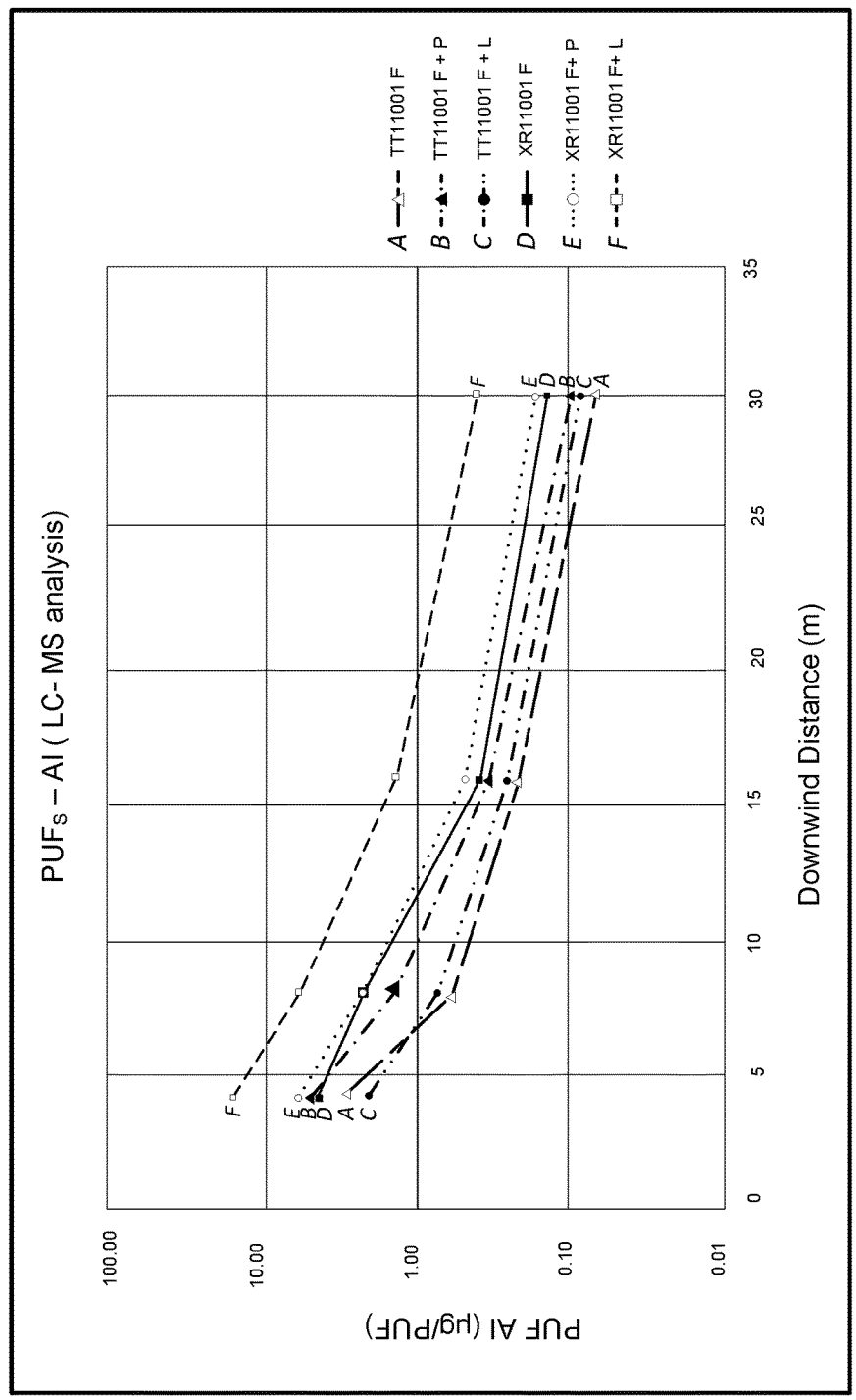
FIG. 8 illustrates a graph 800 of the amount of active ingredient measured on the PUF samples for the study described herein.

FIG. 8 illustrates a graph 800 of the amount of active ingredient measured on the PUF samples for the same tests outlined above. The PUF measurements include the active ingredient collected from spray drift (droplets) and volatilization (vapors). The plot points illustrated in the graph 800 are taken from the data points illustrated in the table 500 of FIG. 5.

Figure 9:
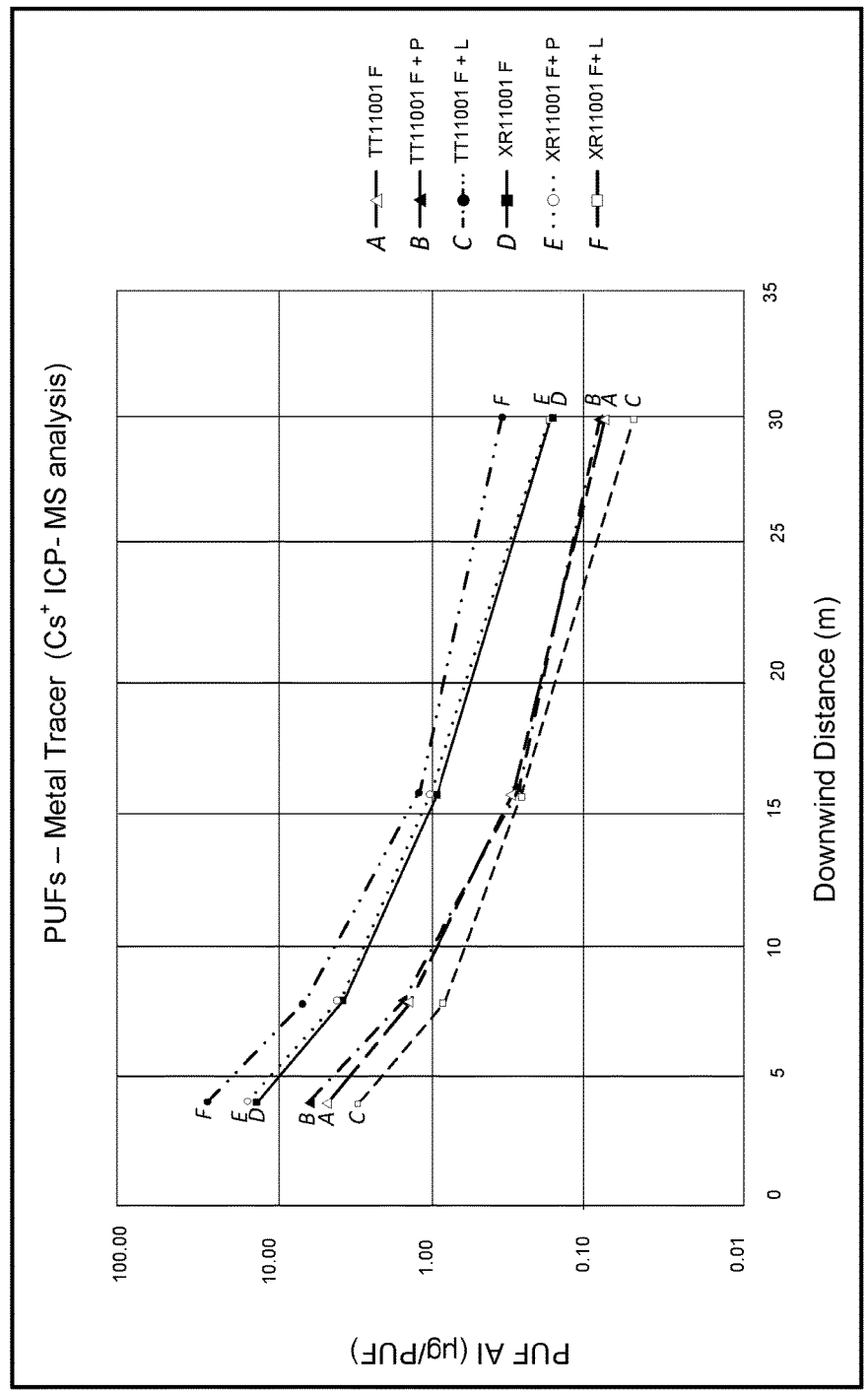
FIG. 9 illustrates a graph 900 of the amount metal tracer measured on the PUF samples for the study described herein.

FIG. 9 illustrates a graph 900 of the amount metal tracer measured on the PUF samples for the same tests outlined above. The PUF measurements include only the metal tracer from spray drift (droplets). The metal tracer does not volatilize. The plot points illustrated in the graph 900 are taken from the data points illustrated in the table 500 of FIG. 5.

Figure 10:
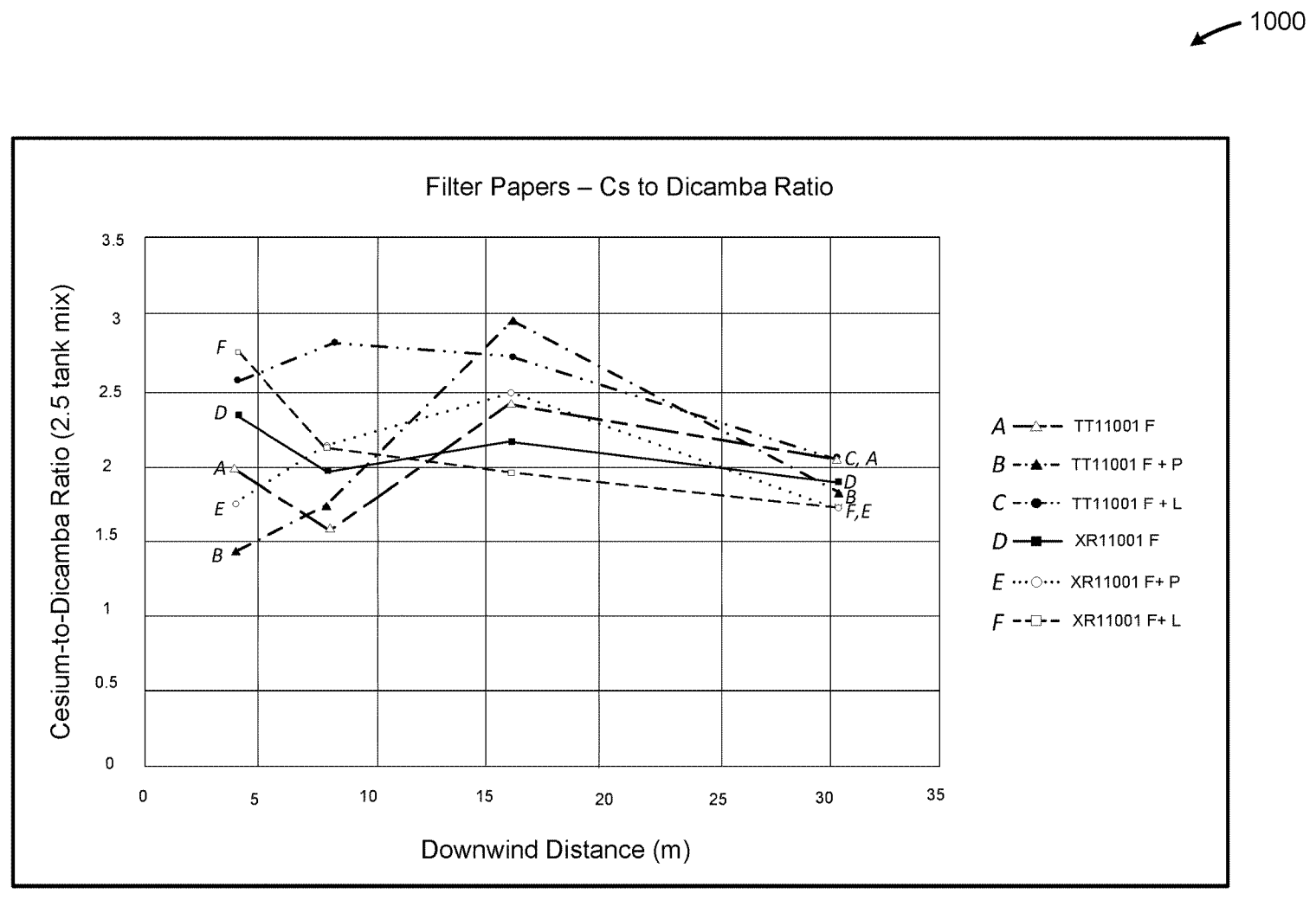
Figure 11:
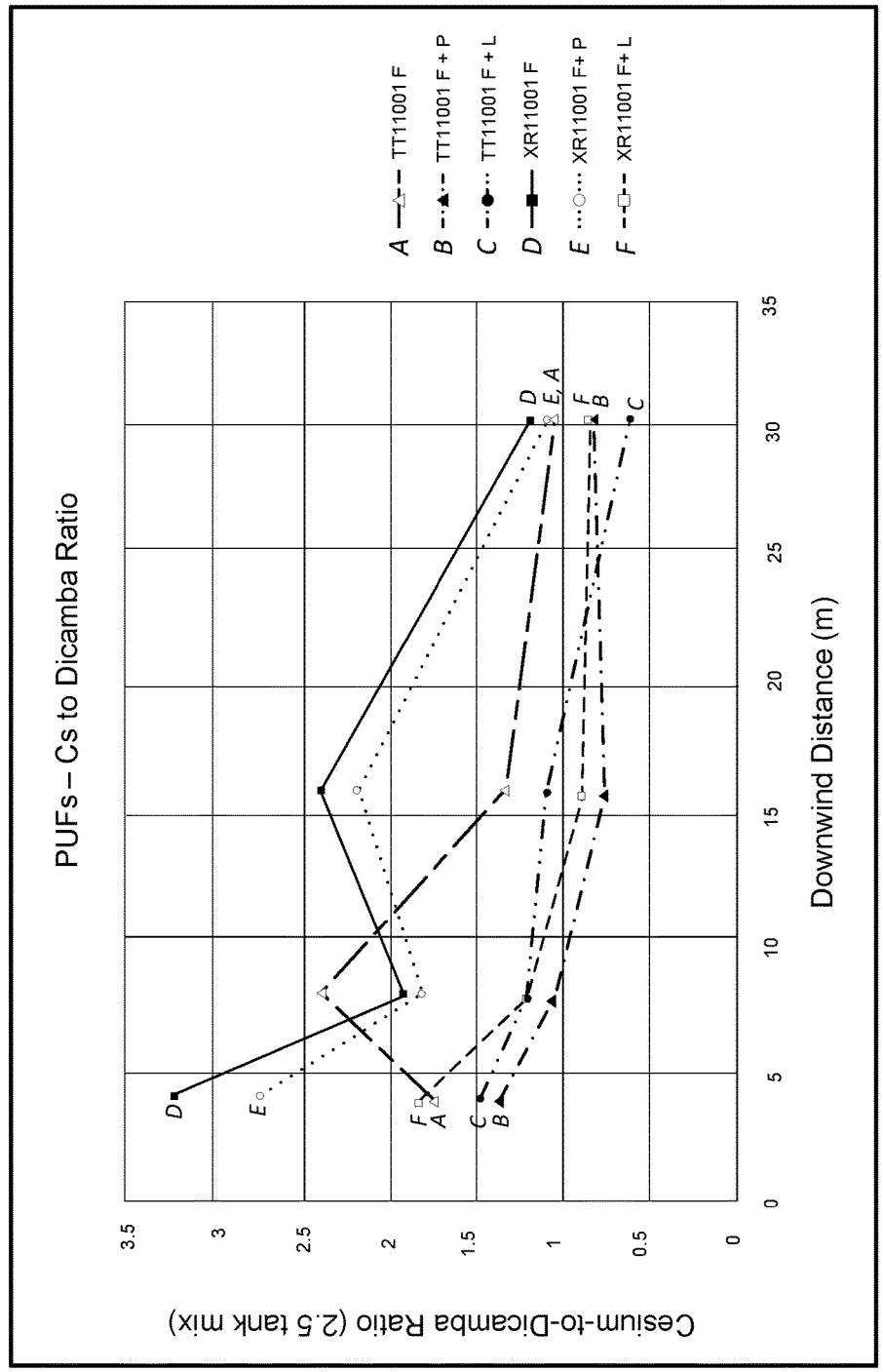
FIG. 11 illustrates a graph 1100 of the ratio of metal tracer to active ingredient amounts collected on the PUFs after 24 hours of exposure/application of AI for the study described herein.

FIG. 10 illustrates a graph 1000 of the ratio of metal tracer to active ingredient amounts collected on the filter papers for the tests described above, taken after the application stage and before the volatility measurements. The filter papers should only include spray drift results—where the ratio in the tank mix was 2.5 metal-to-AI. The graph 1000 generally illustrates that the ratio remained fairly consistent across the samples and at each sample location FIG. 11 illustrates a graph 1100 of the ratio of metal tracer to active ingredient amounts collected on the PUFs after 24 hours of exposure/application of AI for the tests described above. For tests with higher AI volatilization, the ratio of metal-to-AI should decrease as more AI is present from volatilization, e.g., the metal content should remain constant while the proportion of AI increases. Consider a simple example where the tank mix is 1:2 metal to AI. In this example, high volatility of AI could result in a measured ratio of 1:5, or 20%, following the drift measurement stage, which is a substantial decrease from the initial 50% mix and indicative of high volatility. The example percentages/ratio are provided for purposes of illustration and not limitation.

FeXapan on its own should have the lowest volatility. The addition of PowerMax will increase volatility and the addition of Liberty should result in the highest volatility. The result generally follow those trends—but are influenced by the differing atmospheric conditions of each test.

Thus, the present disclosure provides a testing technique to determine if drift of semi-volatile pesticides is due to spray drift, volatility, or both. During an application, spray droplets can drift off target. Once applied to a field, the AI could volatilize and drift off target. It is generally difficult to determine if off-target damage was due to spray drift or volatility. The addition of a tracer, and preferably a metal tracer, to the tank mix provides a way to determine whether the detected AI on a sampler was from spray drift or volatility.

Thus, an empirical study of drift issues for a given application of an AI can be achieved in a wind tunnel in lieu of a large field study. The use of a tracer allows for the driftable AI to be quantified as being from spray drift or volatility. This can help users of spray solutions to tweak formulations to reduce volatility or to assist in better application guidelines to reduce spray drift.

Aspects of the present disclosure have recognized that by adding a tracer, and preferably a metal tracer, to the tank mix/spray solution, the off-target movement can be determined to be due to either spray drift or volatility. Since the metal tracer cannot evaporate, the ratio of metal-to-AI on downwind samplers can be used determine if drift via volatility has occurred. If the ratio is the same as the ratio in the tank mix, detected drift was likely due to spray drift. If there is no metal tracer in a given sample, detected drift was likely associated with volatility. In between those extremes means there is drift due to both spray drift and volatility collected on each sampler.

From the foregoing it will be appreciated that, although specific examples have been described herein for purposes of illustration, various modifications may be made without deviating from the spirit and scope of the disclosure described herein. Accordingly, the disclosure is not limited except as by corresponding claims and the elements recited by those claims. In addition, while certain aspects of the disclosure may be presented in certain claim forms at certain times, the inventors contemplate the various aspects of the disclosure in any available claim form. For example, while only some aspects of the disclosure may be recited as being embodied in a computer-readable medium at particular times, other aspects may likewise be so embodied.

What is claimed is:

1. A method for determining volatility of a spray solution using an agricultural drift tunnel having a blower to generate airflow within the agricultural drift tunnel and a sprayer for projection of the spray solution within the agricultural drift tunnel, the method comprising:
   causing, by the blower, a first target windspeed to be introduced into the agricultural drift tunnel during a first period of time;
   projecting, by the sprayer, the spray solution during the first period of time, the spray solution having predetermined ratio of an active ingredient and a tracer;
   causing, by the blower, a second target windspeed to be introduced into the agricultural drift tunnel during a second period of time, the second period of time being subsequent to the first period of time; and
   determining, after the second period of time, an amount of volatilized active ingredient based on a measured ratio of active ingredient to tracer using at least one sampler disposed within the agricultural drift tunnel.

2. The method of claim 1, wherein the predetermined ratio of active ingredient to tracer in the spray solution is 2.5:1.

3. The method of claim 1, wherein the predetermined ratio of active ingredient to tracer in the spray solution is in a range of 2.0:1.0 to 3.0:1.0.

4. The method of claim 1, wherein the active ingredient of the spray solution comprises a herbicide.

5. The method of claim 1, wherein the active ingredient of the spray solution comprises 3,6-dichloro-2-methoxybenzoic acid (dicamba).

6. The method of claim 5, wherein the dicamba is a Diglycolamine salt or a Dimethylamine salt.

7. The method of claim 1, wherein the tracer comprises a metal.

8. The method of claim 1, wherein the tracer comprises a metal salt.

9. The method of claim 8, wherein the tracer comprises Cesium Chloride (CsCl.

10. The method of claim 1, further comprising disposing at least one filter within the agricultural drift tunnel during the first period of time, the at least one filter configured to collect droplets of the spray solution during the first period of time.

11. The method of claim 10, further comprising determining a baseline measurement based on the at least one filter, the baseline measurement being a ratio of projected active ingredient to tracer after the first predetermined period of time has elapsed.

12. The method of claim 11, wherein determining the baseline measurement based on the at least one filter includes utilizing liquid chromatography-mass spectrometry (LC-MS) to determine an amount of active ingredient present in the at least one filter and inductively coupled plasma mass spectrometry (IC-MS) to determine an amount of tracer present in the at least one filter.

13. The method of claim 10, wherein the at least one filter is disposed adjacent the at least one sampler.

14. The method of claim 10, wherein the at least one filter is disposed at a first predetermined distance from a ground surface within the agricultural drift tunnel, and the at least one sampler is disposed at a second predetermined distance from the at least one filter, the first predetermined distance being less than the second predetermined distance.

15. The method of claim 10, wherein the at least one filter is disposed below the at least one sampler such that the at least one filter is disposed between the at least one sampler and a ground surface within the agricultural drift tunnel.

16. The method of claim 1, wherein the at least one sampler comprises a plurality of samplers, each sampler of the plurality of samplers disposed at a predetermined distance from the sprayer within the agricultural drift tunnel.

17. The method of claim 1, wherein the at least one sampler comprises a Polyurethane Foam (PUF) sampler.

18. The method of claim 17, further comprising generating suction at an orifice of the at least one sampler using a vacuum pump during the second of period of time.

19. The method of claim 18, wherein generating suction at the orifice of the at least one sampler further includes generating at least 1 liters-per-minute (LPM) of air flow.

20. The method of claim 19, wherein generating suction at the orifice of the at least one sampler comprises generating suction in a range of 1.0 LPM to 2.0 LPM.

21. The method of claim 1, further comprising disposing a plurality of samplers including the at least one sampler at predetermined locations along the agricultural drift tunnel and a plurality of filters adjacent the plurality of samplers such that each sampler of the plurality of samplers includes at least one adjacent filter.

22. The method of claim 21, further comprising ceasing projection of the spray solution by the sprayer after the first period of time elapses and removing the plurality of filters to determine a baseline measurement that includes a ratio of active ingredient to tracer.

23. The method of claim 22, wherein determining the baseline ratio of active ingredient to tracer includes averaging measurements from each of the plurality of filters.

24. The method of claim 22, further comprising causing the plurality of samplers to collect volatile vapor during the second period of time.

25. The method of claim 24, wherein causing the plurality of samplers to collect volatile vapor during the second period of time further includes generating suction at an orifice of each of the plurality of samplers based on a vacuum pump.

26. The method of claim 25, wherein introducing suction at an orifice of each of the plurality of samplers further comprises introducing an equal amount of suction at each orifice of the plurality of samplers.

27. The method of claim 26, wherein determining the amount of volatilized active ingredient further comprises determining a ratio of active ingredient to tracer based on the plurality of samplers after the second period of time elapses and comparing the determined ratio to the ratio of the baseline measurement.

28. The method of claim 1, wherein the first target windspeed is greater than the second target windspeed.

29. The method of claim 1, wherein the first target windspeed is at least 10 miles per hour (MPH) and the second target windspeed is 5 MPH or less.

* * * * *